(12) United States Patent
Henegar

(10) Patent No.: US 6,723,729 B2
(45) Date of Patent: Apr. 20, 2004

(54) COMPOUNDS USEFUL IN PREPARING CAMPTOTHECIN DERIVATIVES

(75) Inventor: Kevin E. Henegar, Portage, MI (US)

(73) Assignee: Pharmacia and Upjohn Company, Kalamazoo, MI (US)

(*) Notice: Subject to any disclaimer, the term of this patent is extended or adjusted under 35 U.S.C. 154(b) by 0 days.

(21) Appl. No.: 10/414,852

(22) Filed: Apr. 16, 2003

(65) Prior Publication Data

US 2004/0048832 A1 Mar. 11, 2004

Related U.S. Application Data

(60) Provisional application No. 60/373,727, filed on Apr. 17, 2002.

(51) Int. Cl.[7] ............... A61K 31/445; A61K 31/44; C07D 513/00; C07D 211/08
(52) U.S. Cl. ............ 514/283; 514/316; 546/48; 546/191
(58) Field of Search ............ 546/48, 191; 514/283, 514/316

(56) References Cited

U.S. PATENT DOCUMENTS 6,121,451 A    9/2000   Henegar et al. ............ 546/92

OTHER PUBLICATIONS

Josien et al. (1998) A general synthetic approach to the (20S)–camptothecin family of antitumor agents by a regio controlled cascade radical cyclization of aryl isonitriles. Chemistry—A European Journal 4(1), 67–83.

*Primary Examiner*—D. Margaret Seaman
*Assistant Examiner*—Raymond Covington
(74) *Attorney, Agent, or Firm*—Jonathan P. O'Brien; James C. Forbes

(57) ABSTRACT

Novel compounds are provided having the formula

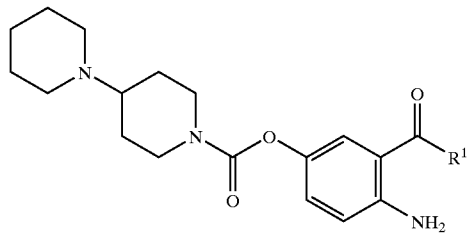

and salt thereof, where $R^1$ is hydrogen, an alkyl, aralkyl, hydroxymethyl, carboxymethyl acyloxymethyl or trialkylsilyl group, or a group —$CH_2NR^3R^4$ where N is a linking nitrogen atom and where (a) $R^3$ and $R^4$ are independently selected from hydrogen and alkyl, alkenyl, hydroxyalkyl and alkoxyalkyl groups; (b) $R^3$ is hydrogen or an alkyl, alkenyl, hydroxyalkyl or alkoxyalkyl group, and $R^4$ is —$COR^5$ where $R^5$ is hydrogen or an alkyl, alkenyl, hydroxyalkyl or alkoxyalkyl group; or (c) $R^3$ and $R^4$ taken together with the linking nitrogen atom form a saturated 3- to 7-member heterocyclic group. These compounds are useful intermediates in a process to prepare camptothecin derivatives including the anti-cancer drug irinotecan.

10 Claims, No Drawings

COMPOUNDS USEFUL IN PREPARING CAMPTOTHECIN DERIVATIVES

This application claims priority of U.S. provisional application Serial No. 60/373,727 filed on Apr. 17, 2002.

FIELD OF THE INVENTION

The present invention relates to manufacture of camptothecin derivatives therapeutically useful as anti-cancer drugs, in particular the camptothecin derivative irinotecan and salts thereof. More particularly, the invention relates to a novel intermediate and to a process for preparing a camptothecin derivative via that intermediate.

BACKGROUND OF THE INVENTION

U.S. Pat. No. 6,121,451 to Henegar & Sih, incorporated herein by reference, discloses a process for preparing the antineoplastic drug irinotecan, also known as 7-ethyl-10-hydroxycamptothecin 10-[1,4'-bipiperidine]-1'-carboxylate or CPT-11 free base. In the disclosed process, a compound therein identified as 14CPT (I) is first reacted with 1-(4-hydroxy-2-aminophenyl)-1-propanone (II) to form an intermediate compound (III), which is then reacted with 4-piperidinopiperidinecarbamyl chloride (IV) to produce CPT-11 free base (V), as shown schematically below.

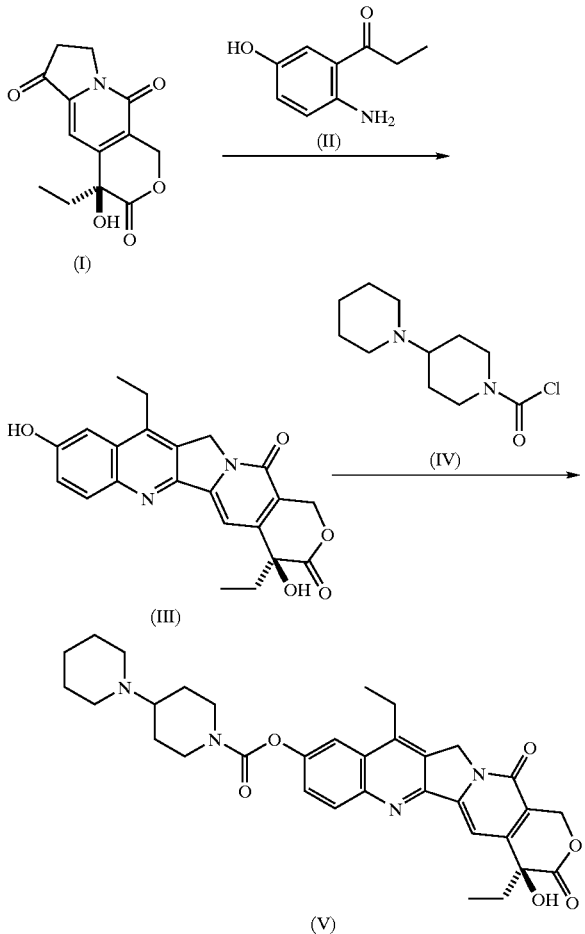

Alternative materials and methods for preparing irinotecan and other therapeutically useful camptothecin derivatives are desired in the art.

SUMMARY OF THE INVENTION

Novel compounds are now provided, having the formula (VI)

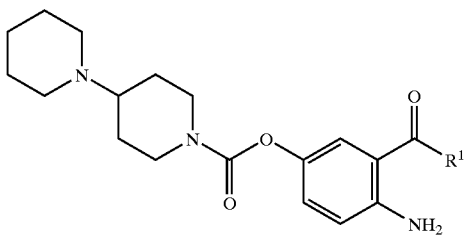

where $R^1$ is hydrogen, an alkyl aralkyl, hydroxymethyl, carboxymethyl, acyloxymethyl or trialklsilyl group, or a group —$CH_2NR^3R^4$ where N is a linking nitrogen atom and where $R^3$ and $R^4$ are as defined hereinbelow. Also provided are salts of the compounds of formula (VI) with pharmaceutically acceptable anions.

Options for $R^3$ and $R^4$ are:
  (a) $R^3$ and $R^4$ are independently selected from hydrogen and alkyl, alkenyl, hydroxyalkyl and alkoxyalkyl groups;
  (b) $R^3$ is hydrogen or an alkyl, alkenyl, hydroxyalkyl or alkoxyalkyl group, and $R^4$ is —$COR^5$ where $R^5$ is hydrogen or an alkyl, alkenyl, hydroxyalkyl or alkoxyalkyl group; or
  (c) $R^3$ and $R^4$ taken together with the linking nitrogen atom form a saturated 3- to 7-member heterocyclic group.

Compounds of the invention are useful intermediates in a process to prepare camptothecin derivatives of formula (VII)

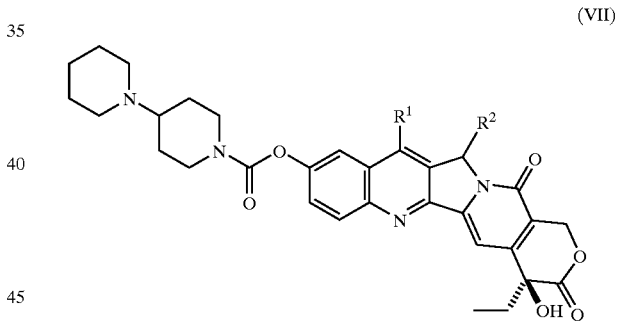

where $R^1$ is as defined above and $R^2$ is hydrogen or an alkyl group, preferably hydrogen.

In a preferred embodiment $R^1$ is an ethyl group and $R^2$ is hydrogen. According to this embodiment, the novel compound of formula (VI) is 4-amino-3-propionylphenyl-1,4'-bipiperidine-1'-carboxylate, which is a useful intermediate in a process to prepare irinotecan (V) and salts thereof, for example the hydrochloride salt CPT-11. Thus, according to another embodiment of the invention, a process is provided comprising a step of reacting 4-amino-3-propionylphenyl-1,4'-bipiperidine-1'-carboxylate with the compound of formula (I) above to form irinotecan.

In yet another embodiment of the invention, a process is provided for preparing a compound of formula (VI). This process can be illustrated with respect to the compound of formula (VI) where $R^1$ is an ethyl group, i.e., 4-amino-3-propionylphenyl-1,4'-bipiperidine-1'-carboxylate. In this case the process comprises a step of reacting 1-(4-hydroxy-2-aminophenyl)-1-propanone (II) with 4-piperidinopiperidinecarbamyl chloride (IV) to form 4-amino-3-propionylphenyl-1,4'-bipiperidine-1'-carboxylate. By appropriate modification of compound (II) one of skill in the art will be able to make other compounds of formula (VI) of the invention.

Typically, an irinotecan or CPT-11 product prepared by a process using 4-amino-3-propionylphenyl-1,4'-bipiperidine-1'-carboxylate will contain at least a detectable amount of that compound. Thus, in yet another embodiment of the invention, there is provided a pharmaceutical composition comprising a therapeutically effective amount of irinotecan and/or a salt thereof and at least a detectable amount of 4-amino-3-propionylphenyl-1,4'-bipiperidine-1'-carboxylate and/or a salt thereof. By its presence in a detectable amount, 4-amino-3-propionylphenyl-1,4'-bipiperidine-1'-carboxylate is useful as an analytical marker for a product of (a) a process involving that compound as a reagent or (b) a process involving as reagents 1-(4-hydroxy-2-aminophenyl)-1-propanone and 4-piperidinopiperidinecarbamyl chloride under circumstances permitting these reagents to react to form 4-amino-3-propionylphenyl-1,4'-bipiperidine-1'-carboxylate.

DETAILED DESCRIPTION OF THE INVENTION $R^1$ in a compound of formula (VI) of the present invention is hydrogen, an alkyl, aralkyl, hydroxymethyl, carboxymethyl, acyloxymethyl or trialkylsilyl, e.g., trimethylsilyl, group, or a group —$CH_2NR^3R^4$ where N is a linking nitrogen atom and where (a) $R^3$ and $R^4$ are independently selected from hydrogen and alkyl alkenyl, hydroxyalkyl and alkoxyalkyl groups; (b) $R^3$ is hydrogen or an alkyl, alkenyl, hydroxyalkyl or alkoxyalkyl group, and $R^4$ is —$COR^5$ where $R^5$ is hydrogen or an alkyl, alkenyl, hydroxyalkyl or alkoxyalkyl group; or (c) $R^3$ and $R^4$ taken together with the linking nitrogen atom form a saturated 3- to 7-member heterocyclic group. Also provided are salts of the compounds of formula (VI) with pharmaceutically acceptable anions.

Alkyl, alkenyl, aralkyl, acyl and alkoxy groups herein, unless otherwise defined, have 1–30, preferably 1–18, more preferably 1–6, carbon atoms. In particularly preferred compounds of formula (VI), $R^1$ is a $C_{1-4}$ alkyl, most preferably an ethyl, group.

Compounds of formula (VI) above exist in free base form and in various pharmaceutically acceptable salt forms, which are embodiments of the present invention.

Pharmaceutically acceptable salts of compounds of formula (VI) include without restriction salts of the following acids: hydrochloric, hydrobromic, sulfuric, methanesulfonic, phosphoric, nitric, benzoic, citric, tartaric, fumaric and maleic acids, and mono- and dicarboxylic acids of formula $CH_3$—$(CH_2)_n$—COOH and HOOC—$(CH_2)_n$—COOH where n is 0 to 4, for example malonic acid. The hydrochloride salt is particularly preferred.

In another embodiment of the invention a process is provided comprising a step of reacting 4-amino-3-propionylphenyl-1,4'-bipiperidine-1'-carboxylate (the compound of formula (VI) where $R^1$ is ethyl) or a salt thereof with 14CPT ((4S)-4-ethyl-7,8-dihydro-4-hydroxy-(1H)-pyrano[3,4-f]indolizine-3,6,10(4H)-trione), the compound of formula (I) above, to form irinotecan or the corresponding salt thereof.

This reaction can illustratively be carried out by beating 4-amino-3-propionylphenyl-1,4'-bipiperidine-1'-carboxylate and 14CPT together in a suitable solvent, for example acetic acid. The product of the reaction can then be purified by a suitable chromatographic method and isolated, for example by crystallization from a suitable solvent medium. An illustrative example of a process of this embodiment of the invention is provided below in [@000e]xample 2.

Accordingly, the novel compound 4-amino-3-propionylphenyl-1,4'-bipiperidine-1'-carboxylate or a salt thereof is a useful intermediate in a manufacturing process for irinotecan or a salt thereof.

Optionally, irinotecan or a salt thereof prepared by a process of the invention can be further processed to yield other camptothecin derivatives by methods known in the art. For example, irinotecan prepared as described herein can be subjected to hydrolysis in an acid medium, for example in presence of hydrochloric acid, to yield 7-ethyl-10-hydroxycamptothecin.

In yet another embodiment of the invention a process for preparing 4-amino-3-propionylphenyl-1,4'-bipiperidine-1'-carboxylate is provided, comprising a step of reacting 1-(4-hydroxy-2-aminophenyl)-1-propanone (II) with 4-piperidinopiperidinecarbamyl chloride (IV).

This reaction can illustratively be carried out by mixing known compounds (II) and (IV) together in a suitable solvent, for example pyridine. Alternatively, a solvent system comprising methylene chloride, tetrahydrofuran, acetonitrile or the like together with a suitable base such as triethylamine or diisopropylethylamine can be used as a medium for the reaction. The product of the reaction can then be subjected to isolation and purification steps, illustratively those described in Example 1 below, to yield 4-amino-3-propionylphenyl-1,4'-bipiperidine-1'-carboxylate.

In yet another embodiment of the invention, a pharmaceutical composition or drug substance is provided comprising (a) irinotecan and/or one or more pharmaceutically acceptable salts thereof in a therapeutically effective total amount, and (b) 4-amino-3-propionylphenyl-1,4'-bipiperidine-1'-carboxylate and/or one or more salts thereof in at least a detectable amount. By a "therapeutically effective" amount of irinotecan or salt thereof is meant an amount useful as at least a single dosage amount for treatment of cancer. By a "detectable" amount of 4-amino-3-propionylphenyl-1,4'-bipiperidine-1'-carboxylate is meant a sufficient amount to give positive identification but not necessarily quantitation of the compound by any suitable analytical technique, for example HPLC.

Preferably according to this embodiment, the drug substance comprises not more than about 5%, more preferably not more than about 2.5% and most preferably not more than about 1% by weight of 4-amino-3-propionylphenyl-1,4'-bipiperidine-1'-carboxylate. The presence of 4-amino-3-propionylphenyl-1,4'-bipiperidine-1'-carboxylatein a drug substance of this embodiment is useful as an analytical marker, providing evidence, for example, that the irinotecan with which it occurs has been prepared by (a) a process involving 4-amino-3-propionylphenyl-1,4'-bipiperidine-1'-carboxylate as a reagent (e.g., the process described above and illustrated in Example 2 below) or (b) a process involving as reagents compounds (II) and (IV) under circumstances permitting these compounds to react to form 4-amino-3-propionylphenyl-1,4'-bipiperidine-1'-carboxylate.

EXAMPLES

The following examples illustrate aspects of the present invention but are not to be construed as limitations.

Example 1

4-Amino-3-propionylphenyl-1,4'-bipiperidine-1'-carboxylate

A solution of 3.26 g (19.6 mmol) 2-amino-5-hydroxypropiophenone and 6.97 g (26.1 mmol) 4-piperidinopiperidinecarbamoyl chloride hydrochloride in 35 ml pyridine was stirred at room temperature for 13 hours. The pyridine was then evaporated and 20 ml water and 120 ml ethyl acetate were added. The resulting organic phase was separated and dried over sodium sulfate. The sodium sulfate was removed by filtration and 10 g silica-60 was added to the filtrate, which was stirred to form a slurry. The slurry was loaded onto a column of 20 g silica-60 (230–400 mesh) and eluted with a 95:5 (v/v) methylene chloride/methanol mixture. The resulting product fractions were combined and evaporated to provide a residue, which was then redissolved in a mixture of 20 ml methylene chloride and 50 ml heptane. The resulting solution was evaporated to yield 6.22 g of 4-amino-3-propionylphenyl-1,4'-bipiperidine-1'-carboxylate as a yellow-green solid, melting point 132.0–133.5° C.

$^1$H NMR (400.13 MHz, CDCl$_3$) δ 7.46 (s, 1H) 7.03 (d, 1H, J=8.8 Hz), 6.64 (d, 1H, J=8.8 Hz), 6.2 (s, 2H), 4.35 (s, 2H), 2.95 (q, 2H, J=7.2 Hz), 2.5–2.9 (m, 9H), 1.4–1.7 (m, 8H), 1.20 (t, 3H, J=7.6 Hz).

$^{13}$C NMR (75.47 MHz, CDCl$_3$) δ 204.39, 155.88, 149.69, 142.2, 130.28, 124.84, 119.71, 119.16, 85.91, 64.38, 51.99, 45.72, 34.11, 29.78, 29.16, 27.62, 26.18, 10.33.

IR (KBr) 3455, 3345, 2965, 2953, 2948, 2932, 2913, 2850, 2783, 2749, 1713, 1662, 1587, 1555, 1421, 1285, 1237, 1219, 1184, 1155, 1149, 1128, 793, 753.

Analysis calculated for C$_{20}$H$_{29}$N$_3$O$_3$: C, 66.83; H, 8.13; N, 11.69. Found: C, 66.46; H, 8.04; N, 11.58.

Example 2

Irinotecan

A solution of 4-amino-3-propionylphenyl-1,4'-bipiperidine-1'-carboxylate as prepared in Example 1 (0.359 g, 1.0 mmol) and 14CPT (the compound of formula (I) above) (0.39 g, 1.5 mmol) in 10 ml acetic acid was heated to 115° C. for 22 hours. The resulting mixture was distilled under vacuum to yield a black semisolid residue. The residue was dissolved in a 95:5 (v/v) methylene chloride/methanol mixture and chromatographed on 20 g silica-60 (230–400 mesh), eluting with 95:5 (v/v) methylene chloride/methanol (400 ml) and then 92.5:7.5 (v/v) methylene chloride/methanol (600 ml). The resulting product fractions were combined and evaporated to provide a residue, which was then redissolved in 20 ml methylene chloride and washed with saturated aqueous sodium bicarbonate solution (2×10 ml). The resulting organic phase was dried over sodium sulfate and evaporated. Ethanol was added and the resulting solution concentrated to a volume of 8 ml before being allowed to crystallize overnight. The solids were filtered and dried to yield 0.243 g of irinotecan (CPT-11 free base) as a pale yellow solid.

The irinotecan produced as above (0.216 g) was dissolved in 2 ml water and 0.43 ml 1M HCl and heated to 60° C. to form a yellow solution. This solution was filtered hot over powdered activated carbon (Darco™ G-60) (0.5 g). The filtrate was cooled and seeded with 5 mg irinotecan hydrochloride crystals and allowed to crystallize overnight. The solids were filtered, washed with water (2×1 ml), and suction dried under air to yield 0.123 g of irinotecan hydrochloride trihydrate as pale yellow crystals having a melting point of 259.8° C.

What is claimed is:

1. A compound having the formula

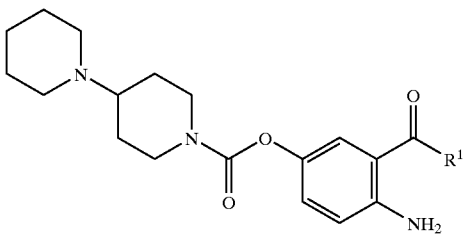

or a pharmaceutically acceptable salt thereof, where R$^1$ is hydrogen, an alkyl, aralkyl, hydroxymethyl, carboxymethyl acyloxymethyl or trialkylsilyl group, or a group —CH$_2$NR$^3$R$^4$ where N is a linking nitrogen atom and where (a) R$^3$ and R$^4$ are independently selected from hydrogen and alkyl, alkenyl, hydroxyalkyl and alkoxyalkyl groups; (b) R$^3$ is hydrogen or an alkyl, alkenyl, hydroxyalkyl or alkoxyalkyl group, and R$^4$ is —COR$^5$ where R$^5$ is hydrogen or an alkyl, alkenyl, hydroxyalkyl or alkoxyalkyl group; or (c) R$^3$ and R$^4$ taken together with the linking nitrogen atom form a saturated 3- to 7-member heterocyclic group.

2. The compound of claim 1 where R$^1$ is an ethyl group.

3. The compound of claim 1 that is a free base form of 4-amino-3-propionylphenyl-1,4'-bipiperidine-1'-carboxylate.

4. The compound of claim 1 that is a salt of 4-amino-3-propionylphenyl-1,4'-bipiperidine-1'-carboxylate with an acid selected from hydrochloric, hydrobromic, sulfuric, methanesulfonic, phosphoric, nitric, benzoic, citric, tartaric, fumaric and maleic acids, and mono- and dicarboxylic acids of formula CH$_3$—(CH$_2$)$_n$—COOH and HOOC—(CH$_2$)$_n$—COOH where n is 0 to 4.

5. The compound of claim 1 that is a hydrochloride salt of 4-amino-3-propionylphenyl-1,4'-bipiperidine-1'-carboxylate.

6. A process for preparing irinotecan or a salt thereof, the process comprising a step of reacting 4-amino-3-propionylphenyl-1,4'-bipiperidine-1'-carboxylate or a salt thereof with the compound having the formula

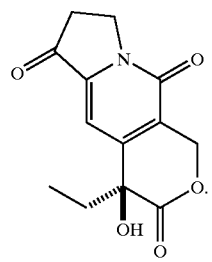

7. Irinotecan or a salt thereof prepared by the process of claim 6.

8. A process for preparing 7-ethyl-10-hydroxycamptothecin or a salt thereof, the process comprising a first step of reacting 4-amino-3-propionylphenyl-1,4'-bipiperidine-1'-carboxylate or a salt thereof with the compound having the formula

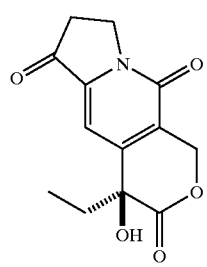

to form irinotecan or a salt thereof; and a second step of hydrolyzing the irinotecan or salt thereof in an acid medium to form 7-ethyl-10-hydroxycamptothecin or a salt thereof.

9. 7-Ethyl-10-hydroxycamptothecin or a salt thereof prepared by the process of claim 8.

10. A process for preparing 4-amino-3-propionylphenyl-1,4'-bipiperidine-1'-carboxylate, the process comprising a step of reacting 1-(4-hydroxy-2-aminophenyl)-1-propanone with 4-piperidinopiperidinecarbamyl chloride.

* * * * *